United States Patent
Markham et al.

(10) Patent No.: US 7,151,260 B2
(45) Date of Patent: Dec. 19, 2006

(54) ANALYZER FOR MEASURING MULTIPLE GASES

(75) Inventors: James R. Markham, Middlefield, CT (US); Peter J. Bonzani, Jr., Manchester, CT (US)

(73) Assignee: Advanced Fuel Research, Inc., East Hartford, CT (US)

( * ) Notice: Subject to any disclaimer, the term of this patent is extended or adjusted under 35 U.S.C. 154(b) by 271 days.

(21) Appl. No.: 10/789,651

(22) Filed: Feb. 27, 2004

(65) Prior Publication Data

US 2004/0227087 A1    Nov. 18, 2004

Related U.S. Application Data

(60) Provisional application No. 60/451,484, filed on Mar. 3, 2003.

(51) Int. Cl.
G01J 5/02 (2006.01)
(52) U.S. Cl. ............ 250/339.08; 250/339.07; 250/339.06
(58) Field of Classification Search ........... 250/339.06, 250/339.07, 339.08
See application file for complete search history.

(56) References Cited

U.S. PATENT DOCUMENTS 4,859,307 A * 8/1989 Nishizawa et al. ......... 204/425

2002/0026822 A1 * 3/2002 Reading et al. ............ 73/31.05
2003/0184733 A1 * 10/2003 Kameoka .................... 356/73
2004/0126624 A1 * 7/2004 Akbar et al. ............... 428/701

OTHER PUBLICATIONS

"The Application of FT-IR Spectroscopy To Turbine Engine Exhaust Measurement", presented Jun. 19-22, 2000.
"Improved Methodology For Turbine Engine Emission Measurements", GT-2002-30606.
Evaluation of The MKS On-Line FTIR Multigas™ Analyzer For Gas Application, Jun. 16-19, 2003.
Oxygen sensing characteristics of limiting current-type sensors with microstructural and structural variations in diffusion barrier, 1996.
"Thin Film air-fuel ratio sensor", 199.
"Limiting current characteristics with regard to oxygen and carbon monoxide in oxidizing and reducing atmospheres", 1996.
"Hydrogen sensing using titania nanotubes", 2003.

* cited by examiner

Primary Examiner—David Porta
Assistant Examiner—Djura Malevic
(74) Attorney, Agent, or Firm—Ira S. Dorman

(57) ABSTRACT

Stand-alone multiple gas analysis apparatus, of relatively small physical size, integrates one or more supplemental sensors, such as a self-heating, amperometric, limiting current-type oxygen sensor and/or a titania nanotube-type hydrogen sensor, into the sampling cell gas flow components of an FT-IR gas analyzer. The apparatus enables simultaneous quantitative concentration measurements of infrared-active gases and of infrared-inactive atomic species and homonuclear diatomic molecules, such as of oxygen and hydrogen.

25 Claims, 6 Drawing Sheets

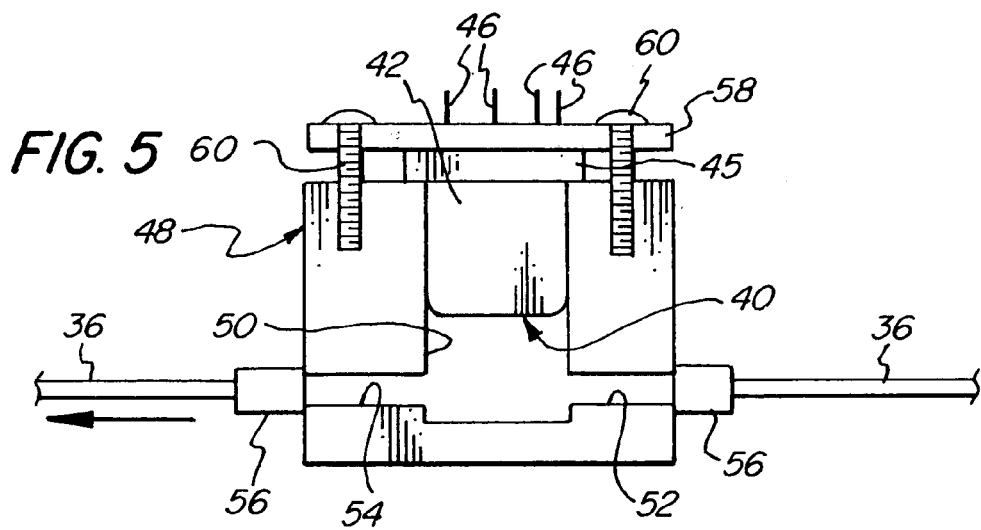
FIG. 5
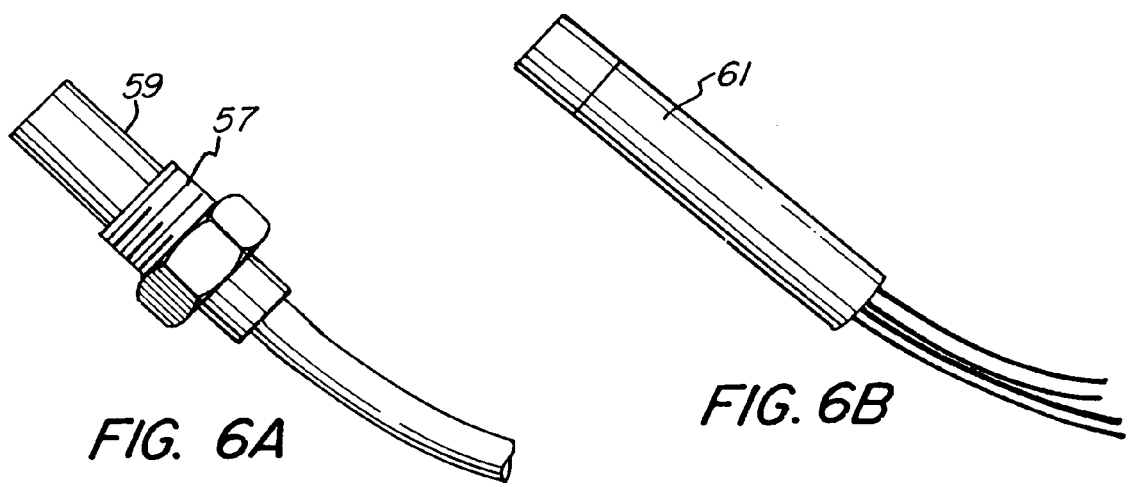
FIG. 6A
FIG. 6B
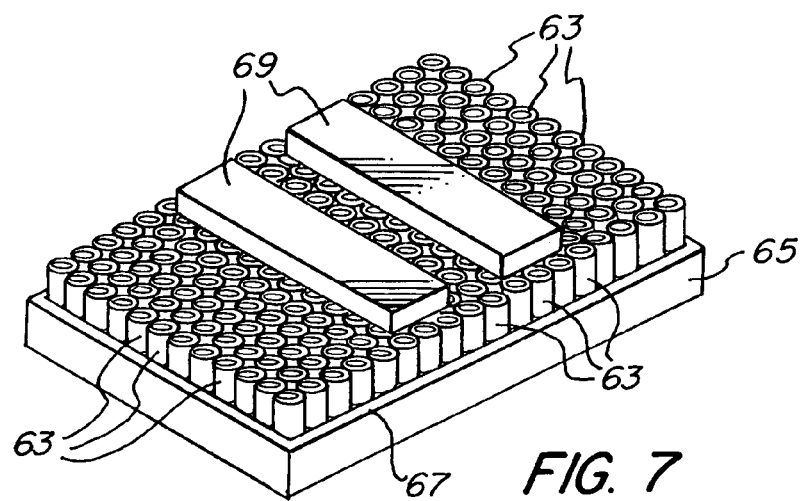
FIG. 7

ANALYZER FOR MEASURING MULTIPLE GASES

CROSS-REFERENCE TO RELATED APPLICATION

This application claims the benefit of U.S. Provisional Patent Application No. 60/451,484, filed Mar. 3, 2003 in the names of the same inventors.

STATEMENT OF GOVERNMENT INTEREST

The United States Government has rights in this invention under Air Force Contract No. F40600-02-C-0018.

BACKGROUND OF THE INVENTION

The measurement of gaseous molecules by Fourier transform infrared (FT-IR) spectroscopy is well known in the art. FT-IR gas analysis is a full spectroscopic technique that makes it possible to monitor many species simultaneously, using a single instrument. It is based on the fact that every gaseous molecule, with the exception of homonuclear diatomics, has a unique set of rotational and vibrational frequencies that absorb and emit infrared energy in a characteristic manner. In general, gases can be identified and quantified based upon the spectral location and magnitude of those absorptions, which occur throughout much of the infrared region of the electromagnetic spectrum. Since FT-IR spectrometers are capable of recording infrared absorptions through the wide wavelength range of about 50 to 1 microns (or, expressed as wavenumbers, about 200 to 10,000 $cm^{-1}$), they can be used to readily identify and quantify an almost unlimited number of different compounds.

FT-IR systems have proven to be a highly effective, space-saving, lower-cost alternative to arrays of single-gas analyzers, which are used, for example, to measure the concentrations of oxygen, water, oxides of carbon, oxides of nitrogen, and total hydrocarbons in engine exhaust gas. In contrast, an FT-IR gas analyzer is capable of simultaneously measuring not only most of those gases but also sulfur dioxide, formaldehyde, ethylene, propylene, methanol, formic acid, nitrous acid, and many others (see Marran, D., Kenny, P., Markham, J., Jalbert, P., Moyers, R., and Gardner, D., "The Application of FT-IR Spectroscopy to Turbine Engine Exhaust Monitoring," AIAA paper 2000-2211 (2000)).

Moreover, the difference in physical size between an FT-IR gas analyzer, and a typical rack of single-gas analyzers used for measuring combustion exhaust gases, is dramatic (see Jalbert, P. and Zaccardi, V., "Improved Methodology for Turbine Engine Emissions Measurement," ASME/IGTI paper no. GT-2002-303606 (2002)). An FT-IR unit will typically occupy a cubic volume that is less than about two feet on a side, whereas a typical assemblage of single-gas analyzers may measure about six feet in height and width, by two to three feet in depth.

Despite the foregoing and other advantages, FT-IR technology is widely recognized to be deficient for multigas analysis applications because of one limitation. As indicated above, FT-IR techniques are unable to detect, and hence to measure, the presence and concentrations of infrared-inactive homonuclear diatomic gases (see Oliver, W., Marran, D. F., Spartz, M. L., Lee, J. C. Y. and Nazeer, W., "Evaluation of the MKS On-Line FTIR MultiGas Analyzer for Gas Turbine Application," ASME/IGTI paper no. GT-2003-38656 (2003)). Eliminating that deficiency, so as to enable the detection and measurement of infrared-inactive gaseous species using a stand-alone, integrated analyzer, is the subject of the present invention.

As one example of an important potential application, the ability to quantitatively measure the excess molecular oxygen concentration in exhaust gas, simultaneously with the combustion-generated emissions, would be of considerable benefit for process understanding, optimization, and control, and when hydrogen is used as a fuel the ability to concurrently measure the concentration of molecular hydrogen would significantly increase the benefit derived. In addition to such combustion process monitoring capability, moreover, the ability to use an FT-IR gas analyzer for ambient air monitoring would enhance safety by providing alarms for warning of hydrogen leaks, of inadequate oxygen concentrations for respiration, and of flammable/combustable conditions at elevated hydrogen levels.

Although the invention is concerned primarily with the measurement of concentrations of molecular oxygen and molecular hydrogen in mixed gas samples (and such applications are therefore emphasized herein), it is also regarded to have application for the detection and measurement of other homonuclear diatomic molecules, such as of gaseous nitrogen, gaseous arsenic, gaseous lithium, and gaseous halogens, as well as for the detection and measurement of gaseous atomic species such as helium, neon, argon and krypton. Applications involving such other molecules and species will be evident to those skilled in the art.

An obvious response to the inability of FT-IR analyzers to measure homonuclear diatomic gases and atomic gases would be to pair FT-IR analyzers with known single-gas analyzers, e.g., for oxygen and/or hydrogen, and the use of a plurality of integrated instruments, rather than a multiplicity of stand-alone units, may be considered attractive from certain standpoints. In addition to being of a size that is still relatively large, however (as compared to a stand-alone FT-IR system), and to entailing relatively high levels of sampling complexity and cost, traditional analyzers with which an FT-IR system might be coupled (e.g., chemical cells, paramagnetic cells, and laser/optical cells used for measuring oxygen) often entail the significant disadvantage of requiring moisture removal from the gas streams being analyzed.

Zirconia-based potentiometric sensors, which function by measuring electric potential and generating an output potential that is related to oxygen partial pressure, are commonly used to analyze automobile exhaust systems, industrial stacks, and the like, for oxygen content. Because they require external heating and the use of a reference gas, however, and provide only a logarithmic output, such potentiometric sensors are regarded to be unsuitable for oxygen-measuring applications to which this invention is addressed.

Traditional hydrogen sensors (e.g., chemical cells such as catalytic bead sensors, semiconductor sensors, electrochemical sensors, resistive palladium alloy sensors, and field effect transistors) also entail significant disadvantages. For example, they tend to be inordinately expensive, to be susceptible to poisoning or chemical irreversibility, and to afford relatively slow response times.

Clearly, the ability to integrate, into an FT-IR system, a capability for measuring infrared-inactive species without increasing overall product dimensions, without requiring the use of dried sample gases, and without unduly increasing cost, complexity, and/or response times, would represent a significant advance in the art. Moreover, the ability for close-coupling, with the optical cell of an FT-IR instrument, of devices for measuring infrared-inactive species would ensure that measurements for all detectable gases were being made concurrently (i.e, at least substantially simultaneously, depending upon the position of the integrated sensor or sensors relative to the FT-IR cell) and from the same, identical gas sample, and thus would promote utmost accuracy in the analysis and provide further nonobvious and significant benefits over the prior art.

SUMMARY OF THE INVENTION

Accordingly, it is the broad object of the present invention to provide an effective system and method, based upon augmented FT-IR technology, for the analysis of mixed gas samples containing infrared-inactive species.

A more specific object is to provide such a system and method that are particularly adapted for the analysis of mixed gas samples containing molecular oxygen and/or molecular hydrogen.

Additional objects of the invention are to provide such a system that is relatively compact, incomplex, inexpensive, and convenient to construct and employ, and to provide such a method that is relatively fast, convenient and effective to perform.

As broadly envisioned, the objects of the invention are attained by the integration of one or more supplemental sensors into an FT-IR product, so as to provide a unitary, stand-alone multiple gas analyzer system that can concurrently measure infrared-inactive species as well as infrared-active molecules, using a single, static or dynamic, gas sample. In operation, the gas-sampling cell of a standard FT-IR analyzer (which will generally be of circular, square or rectangular cross section) constrains a volume of gas for measurement by passage of an infrared beam therethrough, passage taking place along either a straight-through optical path or along a path having an effective length that is increased by internal beam reflection.

More particularly, certain objects of the invention are attained by the provision of a stand-alone multiple gas analysis apparatus comprising: an FT-IR gas analyzer, including a gas sample cell; and at least one supplemental sensor operatively connected to the gas sample cell for generating an electrical signal that is representative of the concentration of at least one infrared-inactive component of a gaseous sample passing through, or contained within, the cell. The apparatus will generally include at least one inlet conduit to the gas sample cell and at least one outlet conduit therefrom, with the supplemental sensor(s) being disposed for effective contact with gases in at least one of the gas sample cell, the inlet conduit, and the outlet conduit.

In preferred embodiments, the electronic data processing means of the FT-IR gas analyzer may be programmed to determine the presence of infrared-active molecules in the gas sample, and will be operatively connected to the sensor, or sensors, for improving the accuracy of gas-concentration data, in the signals generated, by adjusting the data as necessary to account for such infrared-active molecules. The sensors employed in the apparatus will typically comprise a porous ceramic element having electrical properties that vary in relation to the concentration of the infrared-inactive component in effective contact therewith, and will generally include diffusion barriers, which may be of either the pinhole or Knudsen type.

At least one of the supplemental sensors employed in the apparatus will advantageously be a limiting current-type oxygen sensor, which will desirably have integral self-heating means and will preferably employ a porous ceramic sensor element comprised of zirconia. In many instances, a supplemental hydrogen sensor may alternatively, or additionally, be employed in the apparatus, which sensor will advantageously be of the type that exhibits a change in conductance (i.e., reciprocal resistance) in relation to the concentration of molecular hydrogen present. Such a sensor will preferably comprise an array of nanotubes, particularly nanotubes of titania fabrication.

Other objects of the invention are attained by the provision of a method for the analysis of a mixed gas sample containing at least one infrared-active component and at least one infrared-inactive component, wherein the sample is passed into or through the sample cell of an FT-IR gas analyzer; the concentration of the infrared-active component is measured by FT-IR analysis, and the concentration of the infrared-inactive component is concurrently measured by effecting contact of the gas sample with at least one sensor that is operatively connected to the sample cell and is constructed for generating an electrical signal representative thereof.

The method is applicable for measuring the concentrations of homonuclear gaseous diatomic molecules, inclusive of oxygen, hydrogen, nitrogen, arsenic, lithium, and one or more halogens, and also for measuring the concentrations of gaseous atomic species, inclusive of helium, neon, argon and krypton. In more specific, and often preferred, embodiments of the method, the apparatus employed will have at least certain of the additional features set forth herein.

As is well known, the oxygen concentration of a gas can be determined by the limiting current of an electrochemical pumping cell necessarily coupled to either a normal-type (also known as pinhole-type) or Knudsen-type diffusion barrier; indeed, such an amperometric sensor is typically called a "limiting current-type" oxygen sensor. (see Lee, J.-H., Kim, H. and Kim, B. K., "Oxygen Sensing Characteristics of the Limiting Current-Type Sensors with the Microstructural and Structural Variations in Diffusion Barrier," Materials Letters, 26, 27–33 (1996); Kondo, H., Saji, K., Takahashi, H. and Takeuchi, M., "Thin Film Air-Fuel Ratio Sensor," Sensors and Actuators B, 13–14, 49–52 (1993); Lee J-H., Kim, H. and Kim, B. K., "Limiting Current Characteristics with Regard to Oxygen and Carbon Monoxide in Oxidizing and Reducing Atmospheres," Solid State Ionics, 86–88, 1087–1093) (1996)). The gas diffusion mechanism changes from normal—or pinhole-type to Knudsen-type as the pore size of the diffusion barrier is decreased. When the pore diameter is very much larger than the mean free path of gas molecules, as in the pinhole type of barrier, diffusion is not influenced by the pore wall. The frequency of collisions between gas molecules and the pore walls of course increases as the pore size decreases, however, such that, when the pore diameter is almost same order as, or less than, the mean free path of the molecules, Knudsen diffusion becomes predominant.

The oxygen pumping amount through a ceramic element interposed between electrodes is limited by the gas diffusion that occurs above a certain voltage; the current associated with that voltage level is called the "limiting current" ($I_{lim}$), and can be expressed, for the Knudsen-type diffusion barrier, as:

$$I_{\lim} = \left[\frac{4FD_{O_2}SP}{RTl}\right]X_{O_2}$$

where F, $Do_2$, S, P, R, T, l, and $Xo_2$ are, respectively, the Faraday constant, the Knudsen diffusion coefficient of oxygen, the cross-sectional area of the pore in the porous ceramic barrier, the pressure of the gas, the gas constant, the absolute temperature, the length of the pore, and the molar fraction of oxygen in the gas; limiting current values can thus be determined for gaseous samples. For the normal (pinhole)-type diffusion barrier, the limiting current can be expressed as:

$$I_{lim} = -\left[\frac{4FDo_2SP}{RTl}\right](\ln 1 - Xo_2)$$

where $Do_2$ is now the normal diffusion coefficient of oxygen.

Since the electric current through the sensor is proportionally dependent upon the number of oxygen ions pumped across the electrolyte, and since the amount of oxygen diffusing through the barrier is related to the pressure of oxygen in the gas sample, the current output can be calibrated for the oxygen partial pressure; at low oxygen partial pressures, the relationship between the oxygen partial pressure and the output current is linear. In addition to enabling ready measurement of oxygen concentrations in a volume of gas, moreover, the limiting current sensor described is advantageous in requiring no reference gas and also in being available in the form of a miniature, low-cost package (about $100) and with a self-heating feature.

It is well known that nanotubes made of titanium dioxide (also known as titania) offer a property that causes their electrical resistance to decrease in the presence of hydrogen (see Vargese, O. K., Gong, D., Paulose, M., Ong, K. G., and Grimes, C. A., "Hydrogen Sensing Using Titania Nanotubes," Sensors and Actuators B, 93, pp. 338–344 (2003)). This effect results from surface interactions of the hydrogen with the oxygen of the titania crystal structure. In nanotube form (i.e., in the form of crystalline pipes that are only nanometers, or billionths of a meter, wide), the high surface area available in a small sensor package provides a high level of sensitivity to hydrogen. In operation, it is postulated that molecular hydrogen entering an array of titania nanotubes flows about the entire exposed surface, splits into individually charged atoms, and permeates the nanotube surface. The resultant hydrogen ions provide electrons for conductivity, and the change in conductance signals the presence of hydrogen.

Both the limited current-type oxygen sensor and the titania nanotube hydrogen sensor hereinabove described are suitable for integration with an FT-IR gas analysis product. The FT-IR product includes a gas-sampling cell, of finite volume, with means for entry and exit of the sample gas, typically taking the form of tubing measuring less than one-half inch in inside diameter. The oxygen and hydrogen sensors described are of satisfactorily small size to be integrated at one or more of three locations relative to the FT-IR gas sampling cell: 1) at a location at, or prior to entrance of, the gas sampling; 2) at a location in, or in direct communication with, the interior of the gas sampling cell; and 3) at a location at, or post-exit of, the gas sampling cell. Typically, for use in the apparatus of the invention, the integrated sensor unit, including the sensor elements and the supporting structure, will, in broader terms, occupy a volume of about one cubic inch, more or less, and will weigh about a few ounces, more or less. As will be appreciated, the sensor unit will make a negligible contribution to the volume and weight of an FT-IR gas analyzer unit.

Many FT-IR products include an integrated heating system for maintaining the sampling cell, and connected tubing, at elevated temperatures (e.g., 150 degrees Celsius) to avoid condensation of certain sample species; the oxygen and hydrogen sensors employed in the gas analysis apparatus of the invention are well-suited for the heated condition. They are also well-suited for making measurements from both dynamic (i.e., sustained gas sample flow through the FT-IR cell and associated conduits) and also static (i.e., gas sample held at no-flow condition in the FT-IR cell) samples.

In general, gas sensor types that can be effectively integrated into the sample flow path of an FT-IR unit for detection of one or more of the several gaseous atomic, and homonuclear diatomic, infrared-inactive species referred to herein can include those described as: 1) solid oxide electrochemical cell-type sensors; 2) nanomaterial or nanostructure-based sensors, including those utilizing nanotubes and nanoparticles; 3) advanced thin-film microsensors; 4) silicon microelectronic-based sensors; 5) silicon micromachined sensors; 6) microelectromechanical systems (MEMS) sensors; 7) microelectronic sensors utilizing catalyst/absorptive-oxide/insulator/semiconductor in a metal-insulator-semiconductor configuration; and 8) thermal conductivity-type sensors. It will be appreciated that small or miniature gas sensors, adapted for implementing technologies other than those mentioned herein, may exist presently or in the future and may provide the geometrical and functional features necessary for integration with an FT-IR analyzer so as to produce a stand-alone unit capable of identification and quantification of a selected infrared-inactive gaseous molecular or atomic species; all such sensors are deemed to lie within the scope of the claims appended hereto.

BRIEF DESCRIPTION OF THE DRAWINGS

FIG. 5 is a diagrammatic cross-sectional representation of the assembly of FIG. 4;

FIGS. 6A and 6B show additional forms of sensors suitable for use in the apparatus of the invention, the sensor of FIG. 6A comprising a screw-mountable housing and the sensor of FIG. 6B comprising a cylindrical probe, each sensor including a sintered metal cap;

FIG. 7 is a diagrammatic illustration of a nanotube sensor assembly suitable for use in the apparatus of the invention for measuring hydrogen concentrations.

DETAILED DESCRIPTION OF THE PREFERRED AND ILLUSTRATED EMBODIMENTS

Figure 1:
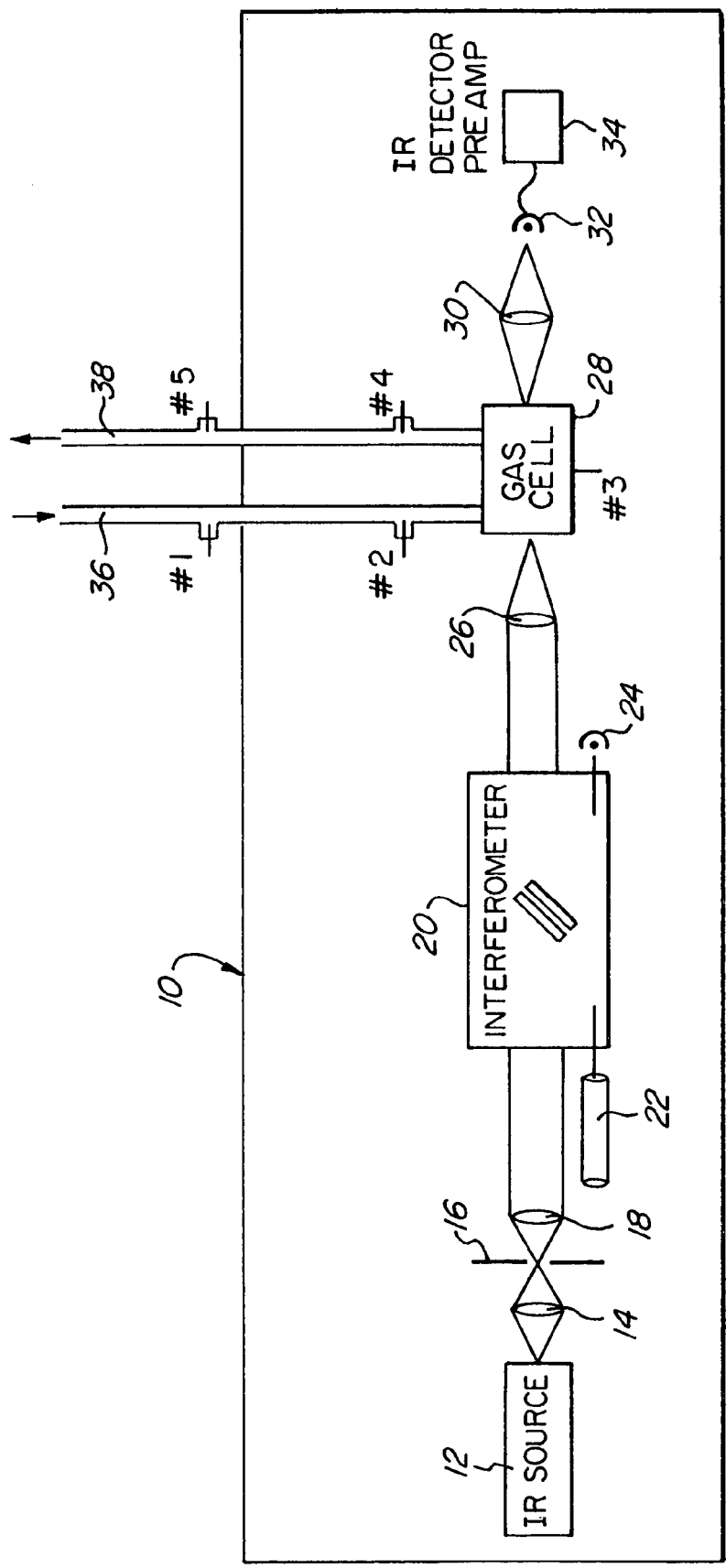
FIG. 1 is a schematic representation of an FT-IR gas analyzer system embodying the present invention.

As seen in FIG. 1, the system of the invention comprises conventional components of an FT-IR gas analyzer contained in a product case, generally designated by the numeral 10. An infrared source 12 projects a beam of radiation sequentially through collection optics 14, a Jacquinot stop 16, and collimation optics 18 to an interferometer 20, the latter being fitted with a laser and a laser detector 22 and 24, respectively. The beam exiting the interferometer 20 passes through collection optics 26 to a gas cell 28, and thereafter through optics 30 to an infrared detector 32, the latter having an associated preamp 34.

Gas entry and exit conduits, or tubes, 36 and 38, lead respectively into and from the FT-IR product gas cell 28. Five suitable locations for the limiting current-type oxygen sensor, employed in the embodiment here described, are indicated and are designated #1 through #5. Specifically, the oxygen sensor may be disposed in the sample inlet transfer tube 36 at location #1, externally of the FT-IR product case 10; it may be disposed in the sample transfer tube 36 at location #2, within the case 10 and upstream of the gas sampling cell 28; it may be installed at position #3, mounted in or on the sampling cell 28 itself; or it may be installed at positions #4 or #5 in the sample exit transfer tube 38, i.e., within the case 10, at a point downstream of the gas sampling cell 28, or externally of the case.

Figure 2:
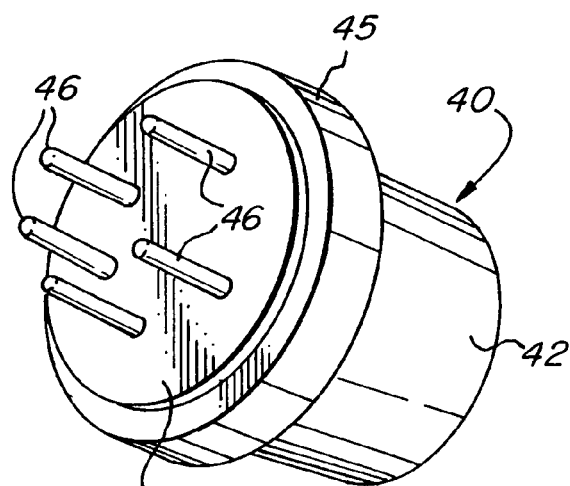
FIG. 2 is a perspective view of a self-heating, amperometric, limiting current-type oxygen sensor suitable for use in the analyzer system of the invention.

FIG. 2 depicts a self-heating, amperometric, limiting current-type oxygen sensor, generally designated by the numeral 40, suitable for use in the present system and comprised of detector elements (not shown in this Figure) enclosed within a Teflon filter 42. As will be appreciated by those skilled in the art, and as is described more fully below, the current-generating component of the sensor may comprise a stack of two porous platinum electrodes lying in intimate, full-surface contact on opposite sides of a porous zirconia ceramic element (electrolyte), with an exterior ceramic element (diffusion barrier) disposed for contact by the sample gas. Pins 46 extend outwardly of the sensor base 44, and provide sensor and heater electrical terminals.

Figure 3A:
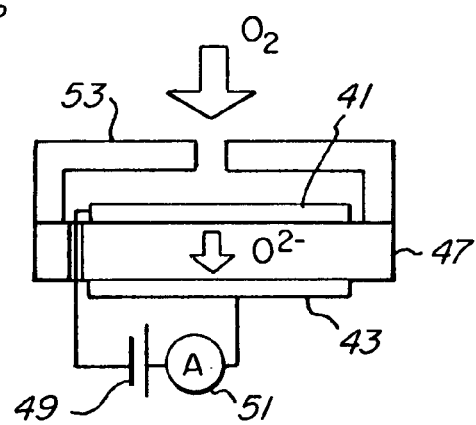
FIGS. 3A and 3B are diagrammatic, cross-sectional views of limiting current-type oxygen sensors having, respectively, a normal-type diffusion barrier and a Knudsen-type barrier.
Figure 3B:
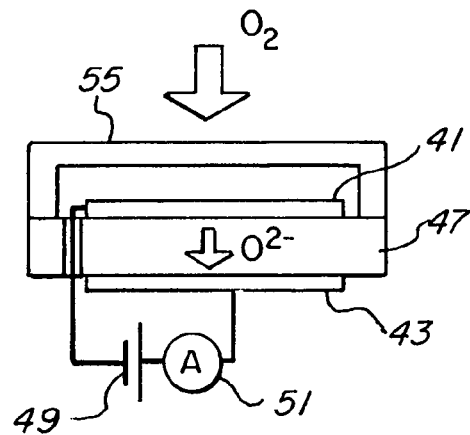

FIGS. 3A and 3B depict limiting current-type oxygen sensors, and show the porous electrodes (cathode 41 and anode 43) on opposite sides of the zirconia electrolyte 47 and connected in an electrical circuit including a cell 49 and an ammeter 51. The sensor of FIG. 3A employs a normal-type, or pinhole-type ceramic diffusion barrier 53; the sensor of FIG. 3B employs a Knudsen-type ceramic barrier 55. As will be appreciated, oxygen diffusing through the barrier 53 or 55, as the case may be, causes the transfer of electrical charge from the cathode 41 to the anode 43 by ionic transport through the electrolyte 47, thus producing an oxygen concentration-indicating current.

Figure 4:
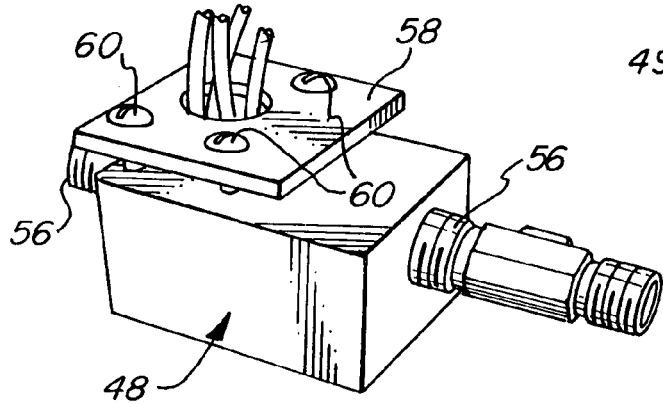
FIG. 4 is a perspective view of an oxygen sensor assembly suitable for integration with an FT-IR multigas analyzer in accordance with the invention.

The sensor described is commercially available as NTK model # MOL005, and has an outside diameter of 19.5 mm (measured at the sensor base 44), and an overall height (inclusive of the pins 46) of about 23 mm. The small size of the sensor enables ready installation directly on the gas sampling cell 28 (i.e., at position #3) simply by providing a small access hole, with the O-ring 45 (or other type sealant) producing a gas-tight seal thereabout; its size also facilitates installation in the gas transfer tubes 36 and 38 (i.e., at locations #1, #2, #4 and #5) as a component of a simple flow-through assembly of the kind depicted in FIGS. 4 and 5.

More particularly, the flow-through assembly consists of a body, generally designated by the numeral 48, defining a sample chamber well 50 to and from which lead inlet and outlet passages 52 and 54, respectively; a threaded tube fitting 56 is engaged in each passage for ready attachment to mating elements on the respective gas flow conduits 36, 38. The sidewall of the body 48 is dimensioned and configured to snugly receive and seat the filter 42 of the sensor 40 within the chamber well 50 (only the filter 42 being seen in FIG. 4), so as to ensure that gas flowing into the lower portion of the chamber will come into intimate contact with the exposed zirconia element of the amperometric sensor component, as described above. A clamp plate 58, secured by fasteners 60, bears upon the base 44 of the sensor and secures it in position with the O-ring 45 (or other sealant) in sealing engagement against the outer surface of the chamber body 48. As will be appreciated, the terminals 46 are suitably wired (as suggested in FIG. 3) to components of the FT-IR analyzer for conducting electrical sensor currents and heater-control signals.

Alternative forms of sensors suitable for use in the apparatus of the invention are depicted in FIGS. 6A and 6B. The sensor of FIG. 6A comprises a screw-mountable housing 57, to which is attached a sintered metal cap 59 enclosing the functional gas species-sensing elements (not shown). Similarly, the sensor of FIG. 6B is in the form of a probe containing the functional elements within a sintered metal cap 61.

The nanotube sensor of FIG. 7 comprises an array of titania nanotubes 63, mounted upon a titanium metal foil base 65 with an insulating barrier layer 67 interposed therebetween to separate the nanotubes 63 from the conducting foil 65. Platinum electrodes 69 are disposed in electrical contact with the free ends of the nanotubes to enable measurement of changes of electrical resistance resulting from the concentration of molecular hydrogen, contained in a multiple gas sample enveloping the nanotube array.

Figure 8A:
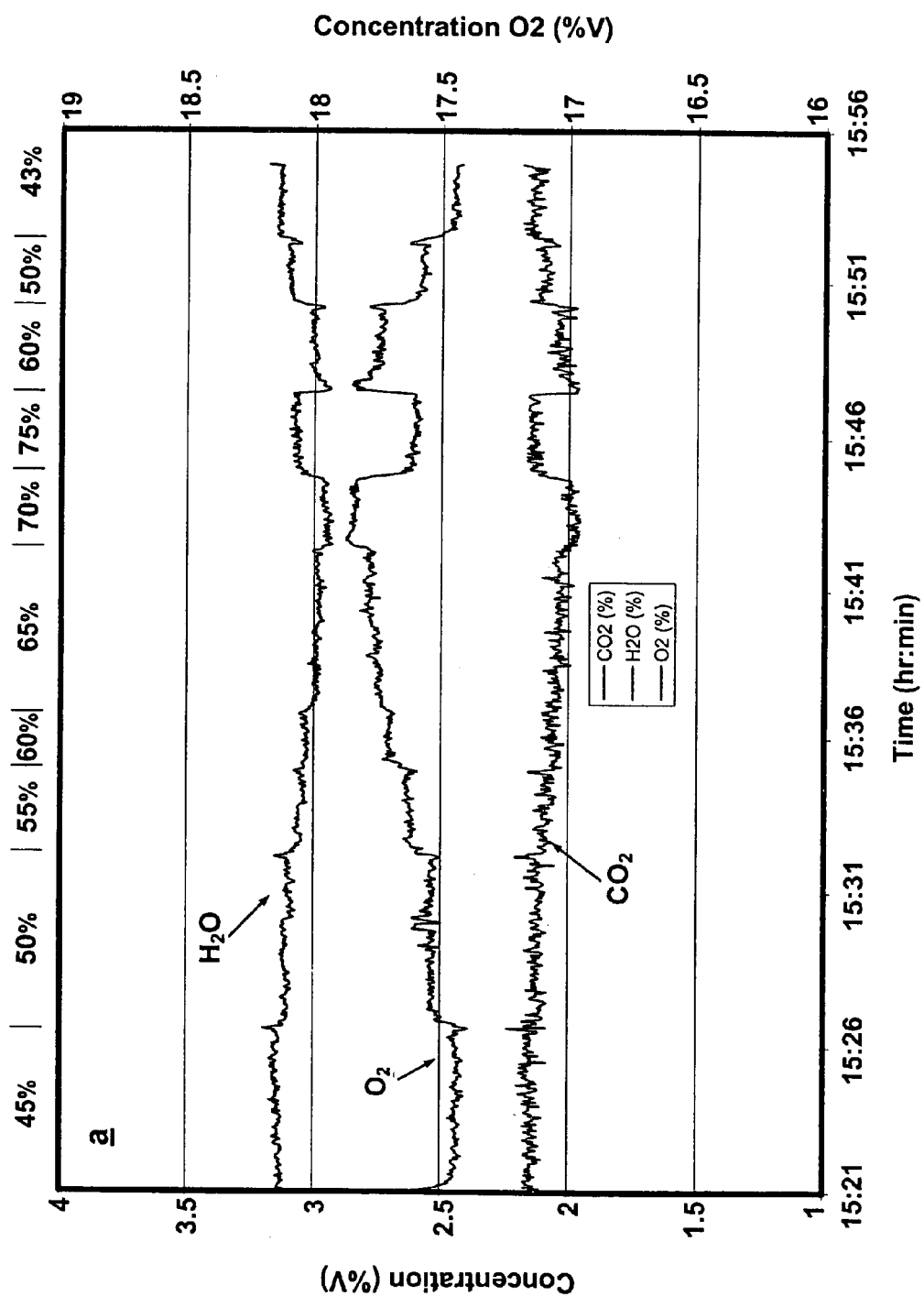
FIG. 8 comprises three plots presenting concentration traces for oxygen and several infrared-active gases measured utilizing the apparatus and methodology of the invention, the mixed-gas sample employed being the exhaust from a turbine engine powered by diesel fuel; wherein engine power is indicated at the top of each plot, excess oxygen concentrations are indicated by the scale at the right of FIG. 8B, and concentrations of all other gases are indicated by the scales at the left in FIGS. 8A, 8B and 8C (the concentration of CO being divided by 100 in 8C).
Figure 8B:
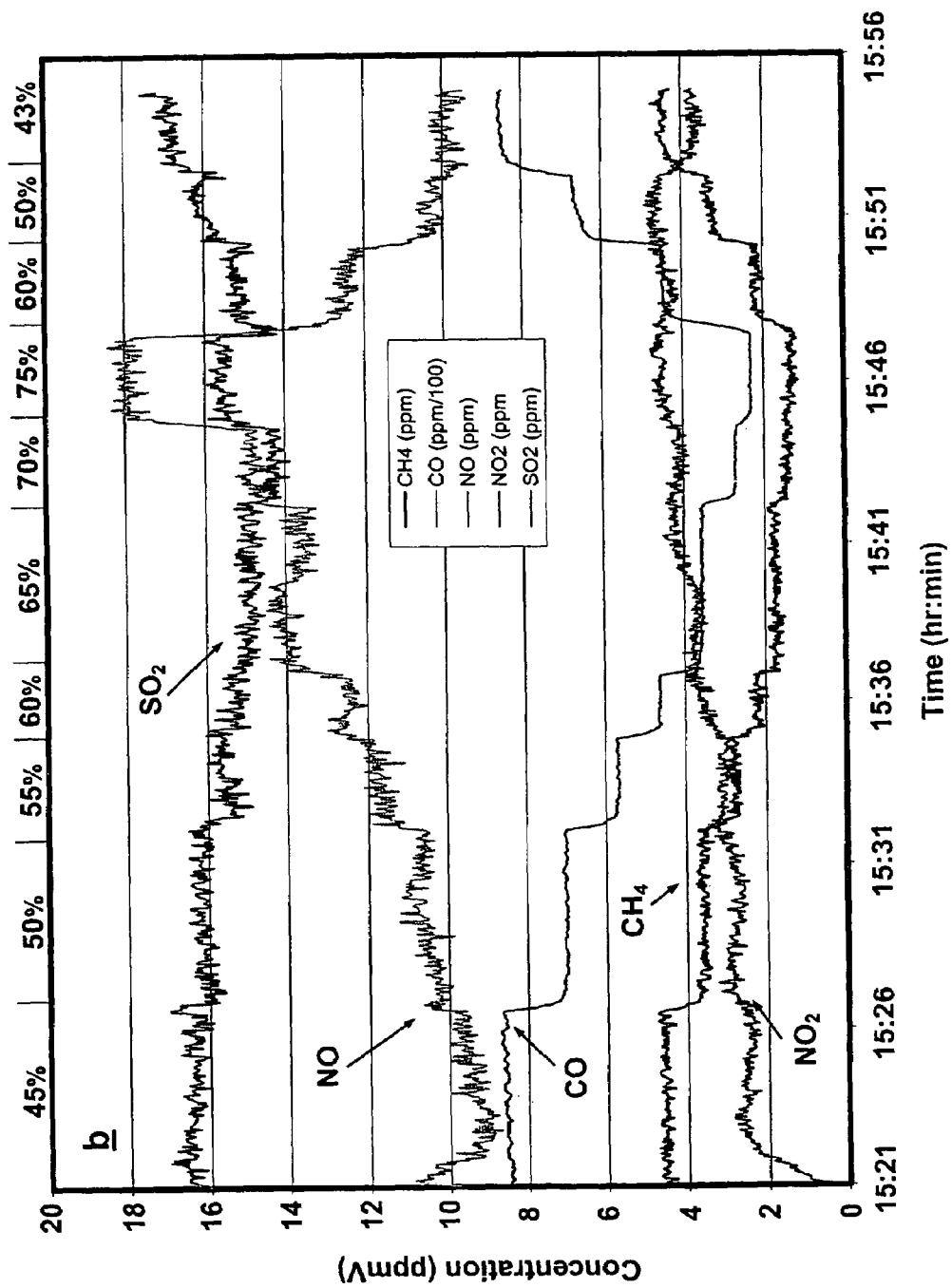
Figure 8C:
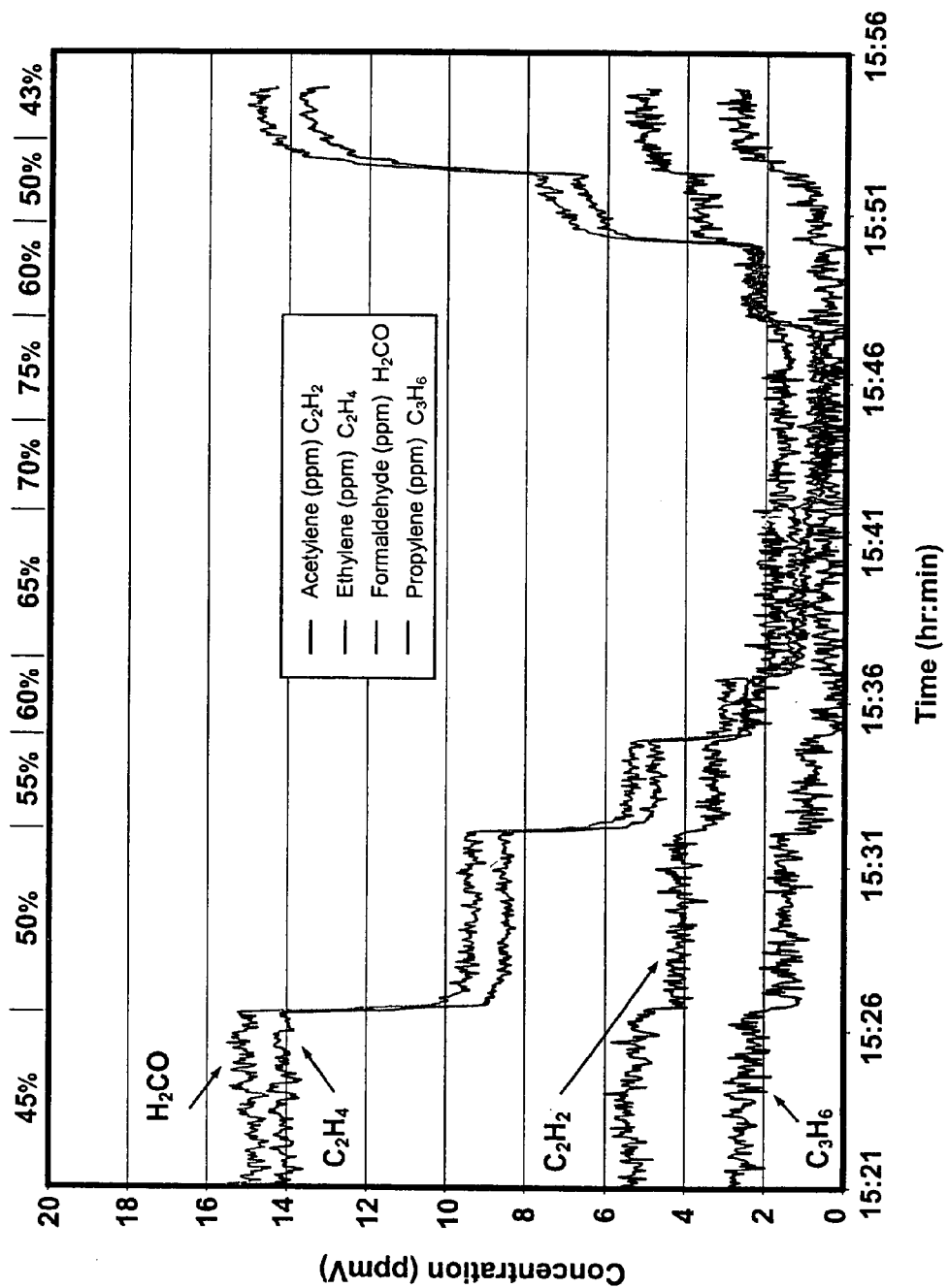

Turning finally to FIG. 8, the plots of which it consists demonstrate the successful measurement of concentrations of molecular oxygen, using apparatus of the kind depicted in FIGS. 1 through 5 hereof, in a multiple gas sample additionally containing water, carbon dioxide, sulfur dioxide, nitric oxide, carbon monoxide, methane, nitrogen dioxide, acetylene, ethylene, formaldehyde and propylene. As pointed out hereinabove, the gas sample constituted the exhaust from a turbine engine powered by diesel fuel.

Infrared-active components of a mixed gas sample will often present significant interference to the sensor for an infrared-inactive gas. Correction to account for such interference can be made through a straight-forward algorithm, which is valid, in the apparatus and method of the present invention, because the gases are measured simultaneously (or at least substantially so) from the same, unique gas sample, thus eliminating sampling differences (i.e., sample temperature, sample pressure, sample residence time in transfer lines) that would occur between separated, individual analyzers. Equations 1 and 2 below exemplify the algorithm, as applied to oxygen and hydrogen measurements respectively, and present the correction for any gas "i" in each case:

$$O_2\%_{(real)} = O_2\%_{(measured)} - ki(i\%_{(measured)}) \quad [1]$$

$$H_2\%_{(real)} = H_2\%_{(measured)} - kii(i\%_{(measured)}) \quad [2],$$

wherein each of the values "ki" and "kii" is a constant specific to gas "i" and can be determined by controlled measurements made using certified gases mixtures (i.e, calibration gases of known, certified concentrations). For example, for a real mixture containing 17% oxygen ($O_2$) and 2.3% carbon dioxide ($CO_2$), ki($CO_2$%)=0.058%, so the $O_2$ reading from the integrated sensor would be in error by 0.3% of the reading, it being noted that the level of error is well within the typical accuracy of certified calibration standards (typically ±2%). However, software algorithms utilizing equations [1] and [2] can be implemented if desired or deemed necessary. It is known that most combustion-generated gases present negligible interference at the parts-per-million levels typically encountered.

Thus, the present invention provides an integrated, unitary, stand-alone multiple gas analyzer that enables measurements (i.e., identification and quantification) of gaseous infrared-inactive molecules, particularly oxygen and hydrogen, and infrared-inactive atomic species, simultaneously with the measurement of a wide variety of infrared-active gaseous molecules. The apparatus has proven effective at temperatures from ambient to 150° C., which temperatures are commonly used in FT-IR gas analyzers so as to avoid fouling of optical surfaces by condensates of certain gases. The apparatus uniquely integrates Fourier transform infrared technology and sensor technology, the FT-IR analyzer providing a gas sampling cell with means for sample entry and exit and the supplemental sensor typically taking the form of a ceramic sensor, exhibiting a change in electrical current for sensing oxygen and exhibiting a change in electrical resistance for sensing hydrogen. A sensor is positioned at one (or more) of five suitable locations relative to the FT-IR gas sampling cell for measuring the diatomic or atomic infrared-active gas species at points upstream or downstream of, or within, the cell. The invention offers particular and significant advantages for measuring process input and exhaust gas mixtures, for measuring ambient air and confined air spaces for environmental and condition safety, and for monitoring leakage from process infrastructure.

Having thus described the invention, what is claimed is:

1. Stand-alone multiple gas analysis apparatus comprising: an FT-IR gas analyzer, including a product case, an infrared radiation source, an interferometer, a gas sample cell, an infrared detector having an associated preamplifier, and optics operatively disposed for transmitting radiation between said radiation source, said interferometer, said gas sample cell and said detector, said radiation source, said interferometer, said gas sample cell, said detector and preamplifier, and said optics all being enclosed within said FT-IR gas analyzer product case, said FT-IR gas analyzer additionally including a single gas inlet conduit connected to said gas sample cell for conducting gas to said gas cell from a location external to said product case and having at least a portion of its length enclosed within said product case, and a single gas outlet conduit connected to said gas sample cell for conducting gas from said gas sample cell to a location external to said product case and having at least a portion of its length enclosed within said product case, said single gas inlet conduit, said single gas outlet conduit, and said gas sample cell cooperatively defining a gas flow path for gas to be analyzed; and at least one sensor, enclosed within said FT-IR product case and integrated into structure defining said gas flow path for contact by the gas to be analyzed, said at least one sensor being constructed for the analysis of molecular oxygen and for generating an electrical signal representative of the concentration of molecular oxygen; said analysis apparatus being devoid of gas analysis means disposed external to said FT-IR gas analyzer product case and operatively connected to said gas flow path for contact by the gas to be analyzed.

2. The apparatus of claim 1 wherein said FT-IR gas analyzer includes electronic data processing means programmed to determine the presence of infrared-active molecules in the gas sample, said electronic data processing means being operatively connected to said at least one sensor for improving the accuracy of gas-concentration data, in the signal from said at least one sensor, by adjusting said data as necessary to account for such infrared-active molecules.

3. The apparatus of claim 1 wherein said at least one sensor comprises a porous ceramic element having electrical properties that vary in relation to the concentration of molecular oxygen in effective contact therewith.

4. The apparatus of claim 3 wherein said at least one sensor comprises a diffusion barrier of either the pinhole or Knudsen type.

5. The apparatus of claim 3 wherein said at least one sensor is a limiting current-type oxygen sensor.

6. The apparatus of claim 5 wherein said at least one sensor has integral self-heating means, and wherein said porous ceramic element thereof comprises zirconia.

7. The apparatus of claim 6 wherein said at least one sensor is located downstream of said gas cell.

8. The apparatus of claim 1 additionally including a second sensor that is constructed for the analysis of molecular hydrogen and for generating an electrical signal representative of the concentration of molecular hydrogen, said second sensor also being enclosed within said FT-IR product case and integrated into said structure defining said gas flow path for contact by the gas to be analyzed.

9. The apparatus of claim 8 wherein said second sensor is a hydrogen sensor of the type that exhibits a change in resistance in relation to the concentration of molecular hydrogen in effective contact therewith.

10. The apparatus of claim 9 wherein said at least one sensor comprises an array of nanotubes.

11. The apparatus of claim 10 wherein said nanotubes are of titania fabrication.

12. A method for the analysis of a mixed gas sample, comprising:
    passing a sample of a mixed gas along a gas flow path into or through the sample cell of an FT-IR gas analyzer, said mixed gas sample containing molecular oxygen and at least one infrared-active component;
    measuring, by FT-IR analysis, the concentration of said at least one infrared-active component in said mixed gas sample; and
    concurrently measuring the concentration of molecular oxygen in said mixed gas sample by effecting contact of said sample with at least one sensor constructed for generating an electrical signal representative of the concentration of molecular oxygen; said FT-IR gas analyzer including a product case, an infrared radiation source, an interferometer, a gas cell, an infrared detector having an associated preamplifier, and optics operatively disposed for transmitting radiation between said radiation source, said interferometer, said gas cell and said detector, said radiation source, said interferometer, said gas cell, said detector and preamplifier, and said optics all being enclosed within said FT-IR gas analyzer product case, said FT-IR gas analyzer additionally including a single gas inlet conduit connected to said gas cell for conducting gas to said gas cell from a location external to said product case and having at least a portion of its length enclosed within said product case, and a single gas outlet conduit connected to said gas cell for conducting gas from said gas cell to a location external to said product case and having at least a portion of its length enclosed within said product case, said single gas inlet conduit, said single gas outlet conduit, and said gas cell cooperatively defining said gas flow path for gas to be analyzed; and at least one sensor, enclosed within said FT-IR product case and integrated into structure defining said gas flow path for contact by the gas to be analyzed, said at least one sensor being constructed for the analysis of molecular oxygen and for generating an electrical signal representative of the concentration of molecular oxygen; said analysis apparatus being devoid of gas analysis means disposed external to said FT-IR gas analyzer product case and operatively connected to said gas flow path for contact by the gas to be analyzed; said sample of mixed gas being passed into contact with no gas analysis means upstream or downstream of said FT-IR gas analyzer along said gas flow path defined therein.

13. The method of claim 12 wherein said FT-IR gas analyzer includes electronic data processing means programmed to determine the presence of infrared-active molecules in said mixed gas sample, said electronic data processing means being operatively connected to said at least one sensor for improving the accuracy of gas-concentration data, in said signal from said at least one sensor, by adjusting said data as necessary to account for such infrared-active molecules.

14. The method of claim 12 wherein said sample of mixed gas is obtained from the exhaust gas of a combustion process.

15. The method of claim 12 wherein said FT-IR gas analyzer additionally includes a second sensor that is constructed for the analysis of molecular hydrogen and for generating an electrical signal representative of the concentration of molecular hydrogen, said second sensor also being enclosed within said FT-IR product case and integrated into said structure defining said gas flow path for contact by the gas to be analyzed.

16. The method of claim 15 wherein said at least one sensor has integral self-heating means, and wherein said second sensor is of the type that exhibits a change in resistance in relation to the concentration of molecular hydrogen in effective contact therewith, and wherein the concentration of molecular hydrogen is measured in said method.

17. The method of claim 16 wherein said second sensor comprises an array of nanotubes.

18. The method of claim 17 wherein nanotubes are of titania fabrication.

19. The method of claim 12 wherein said at least one sensor comprises a porous ceramic element having electrical properties that vary in relation to the concentration of molecular oxygen.

20. The method of claim 19 wherein said at least one sensor comprises a diffusion barrier of either the pinhole or Knudsen type.

21. The method of claim 19 wherein said at least one sensor is a limiting current-type oxygen sensor.

22. The method of claim 21 wherein said at least one sensor has integral self-heating means, and wherein said porous ceramic element of said at least one sensor comprises zirconia.

23. The method of claim 22 wherein said at least one sensor is located downstream of said gas cell.

24. A method for monitoring a combustion process, comprising:

carrying out a combustion process which produces a mixed gas exhaust stream;

obtaining samples from said mixed gas exhaust stream;

passing said samples of mixed gas along a gas flow path through an FT-IR gas analyzer, said mixed gas samples containing molecular oxygen and at least one infrared-active component;

measuring, by FT-IR analysis, the concentration of said at least one infrared-active component in each of said mixed gas samples; and concurrently measuring the concentration of molecular oxygen in each of said mixed gas samples by effecting contact of said sample with at least one sensor constructed for generating an electrical signal representative of the concentration of molecular oxygen; said FT-IR gas analyzer including a product case, an infrared radiation source, an interferometer, a gas cell, an infrared detector having an associated preamplifier, and optics operatively disposed for transmitting radiation between said radiation source, said interferometer, said gas cell and said detector, said radiation source, said interferometer, said gas cell, said detector and preamplifier, and said optics all being enclosed within said FT-IR gas analyzer product case, said FT-IR gas analyzer additionally including a single gas inlet conduit connected to said gas cell for conducting gas to said gas cell from said combustion process and having at least a portion of its length enclosed within said product case, and a single gas outlet conduit connected to said gas cell for conducting gas from said gas cell to a location external to said product case and having at least a portion of its length enclosed within said product case, said single gas inlet conduit, said single gas outlet conduit, and said gas cell cooperatively defining said gas flow path for said samples of mixed gas and at least one sensor, enclosed within said FT-IR product case and integrated into structure defining said gas flow path for contact by said samples of mixed gas, said at least one sensor being constructed for the analysis of molecular oxygen and for generating an electrical signal representative of the concentration of molecular oxygen; said analysis apparatus being devoid of gas analysis means disposed external to said FT-IR gas analyzer product case and operatively connected to said gas flow path for contact by said samples of mixed gas; said samples of mixed gas being passed into contact with no gas analysis means upstream or downstream of said FT-IR gas analyzer along said gas flow path defined therein.

25. The method of claim 24 wherein said FT-IR gas analyzer additionally includes a second sensor that is constructed for the analysis of molecular hydrogen and for generating an electrical signal representative of the concentration of molecular hydrogen, said second sensor also being enclosed within said FT-IR product case and integrated into said structure defining said gas flow path for contact by said samples of mixed gas, and said method measuring the concentration of molecular hydrogen concurrently with said measurements of said at least one infrared-active component and said molecular oxgyen.

* * * * *